United States Patent
Tsukada et al.

(10) Patent No.: US 6,695,831 B1
(45) Date of Patent: *Feb. 24, 2004

(54) CATHETER FOR INTERMITTENT SELF-CONDUCTION OF URINE

(75) Inventors: Osamu Tsukada, Nagano-ken (JP); Yasuhiko Nakajima, Kanagawa-ken (JP)

(73) Assignee: Tsukada Medical Research Co., Ltd., Tokyo (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/679,519

(22) Filed: Oct. 6, 2000

(30) Foreign Application Priority Data

Oct. 6, 1999 (JP) ............................. 11-285092

(51) Int. Cl.⁷ .......................... A61M 27/00; A61M 1/00
(52) U.S. Cl. .......................................... 604/544; 604/27
(58) Field of Search ..................... 604/27, 508, 93.01, 604/171, 181, 184, 164.08, 167.06, 170.03, 192, 256, 264, 273, 274, 523, 544, 347, 349, 524

(56) References Cited

U.S. PATENT DOCUMENTS

| 3,460,540 A | | 8/1969 | Gagne ........................ 128/349 |
| 5,219,337 A | * | 6/1993 | Takata et al. ................ 604/185 |
| 5,242,398 A | * | 9/1993 | Knoll et al. ............. 604/103.05 |
| 5,496,300 A | * | 3/1996 | Hirsch et al. ................ 604/327 |
| 5,531,719 A | * | 7/1996 | Takahashi .................... 604/525 |
| 5,817,067 A | * | 10/1998 | Tsukada ...................... 604/256 |
| 6,264,624 B1 | * | 7/2001 | Desmond, III et al. .......... 604/8 |
| 2002/0002382 A1 | * | 1/2002 | Wallace et al. ............. 606/191 |

FOREIGN PATENT DOCUMENTS

| EP | 0781572 A2 | 2/1997 | .......... A61M/39/02 |
| WO | WO-94/26342 | 11/1994 | .......... A61M/25/01 |
| WO | WO-96/15824 | 5/1996 | .......... A61M/29/00 |
| WO | WO-96/41653 | 12/1996 | .......... A61M/25/01 |

* cited by examiner

Primary Examiner—Brian L. Casler
Assistant Examiner—Matthew F DeSanto
(74) Attorney, Agent, or Firm—Sughrue Mion, PLLC

(57) ABSTRACT

A catheter for intermittent self-conduction of urine which is relatively hard to deflect easy to insert into a body, and eliminate any pain and danger while in the body. A catheter for intermittent self-conduction of urine comprises an urine conduction tube (1) having an urine conduction aperture (13) in a distal end (11) thereof, a holder (3) coupled to a proximal end (12) of the urine conduction tube (1) and adapted to be detachably engaged with an inlet port (22) of a sterilizing solution case (2) which is adapted to contain a sterilizing solution (21), and a cap (4) for closing an outlet (311) of the holder (3). The urine conduction tube (1) is a dual layer tube including an inner tube member (101) made of a hard synthetic resin material which is medicine-proof and an outer tube member (102) made of a soft synthetic resin material which is medicine-proof. The inner tube member (101) in the urine conduction tube (1) is made of a hard synthetic resin material which is medicine-proof and is selected from a group of polytetrafluoroethylene, olefine base resin, polyamide base resin, and polyester base resin. The outer tube member (102) in the urine conduction tube (1) is made of a soft synthetic resin material which is medicine-proof and is selected from a group of silicone rubber, fluororubber, and butyl rubber.

5 Claims, 4 Drawing Sheets

CATHETER FOR INTERMITTENT SELF-CONDUCTION OF URINE

BACKGROUND OF THE INVENTION

This invention relates to a catheter for intermittent self-conduction of urine, which can be used by a person suffering from urinary dysfunction at need.

Where urinary dysfunction exists it may be necessary to carry out urine conduction whereby a catheter is inserted through the urethra into the bladder to discharge urine. Urine conduction can consist of either a temporary method or a continuous method. In the case of disease such as occlusion of a lower urinary tract, neurogenetic bladder, medicine action, psychogenetic anuresis, or the like, urine conduction must be effected intermittently by the patient.

Heretofore, when a flexible catheter is used, it was difficult to insert the catheter from an urethra into an urinary bladder. In this case, a stylet made of a stainless steel was inserted into the catheter to temporarily harden the catheter, such temporarily hardened catheter was inserted into the bladder, and then the stylet was drawn from the catheter. Accordingly, the conventional catheter requires additional steps of inserting the stylet and drawing it. The additional steps are not only inconvenient but also can be unsafe in a narrow toilet In order to make a catheter relatively hard, it was made of a hard synthetic resin material or a metal material. Such an inflexible catheter, while relatively easy to insert, induced pain and tended to damage the urethra.

Accordingly, an object of the present invention is to provide a catheter for intermittent self-conduction of urine which is relatively hard to deflect, easy to insert into a body, and causes neither pain nor damage while in the body.

SUMMARY OF THE INVENTION

A catheter for intermittent self-conduction of urine in accordance with the present invention comprises: an urine conduction tube having an urine conduction aperture in a distal end thereof; a holder coupled to a proximal end of the urine conduction tube and adapted to be detachably engaged with an inlet port of a sterilizing solution case which is adapted to contain a sterilizing solution; and a cap for closing an outlet of the holder. The urine conduction tube is a dual layer tube including an inner tube member made of a hard synthetic resin material which is medicine-proof, and an outer tube member made of a soft synthetic resin material which is medicine-proof.

The inner tube member in the urine conduction tube is made of a hard synthetic resin material which is medicine-proof and is selected from a group of polytetrafluoroethylene (trade name "TEFLON"), olefine base resin, polyamide base resin, and polyester base resin. The outer tube member in the urine conduction tube is made of a soft synthetic resin material which is medicine-proof and is selected from a group of silicone rubber, fluororubber, and butyl rubber. Preferably, the inner tube member made of a hard synthetic resin material which is medicine-proof has a hardness in the range of D 50 to D 90 and a thickness in the range of 0.2 mm to 2.0 mm. The outer tube member made of a soft synthetic resin material which is medicine-proof preferably has a hardness in the range of SH 10 to SH 80 and a thickness in the range of 0.2 mm to 2.0 mm.

The holder may be provided on its upper portion with a handle to be held by a user in use. The holder may be also provided on its lower portion with a case cover which covers inner and outer surfaces of an inlet port in the sterilizing solution case when the urine conduction tube is contained in the sterilizing solution case.

BRIEF DESCRIPTION OF THE DRAWINGS

The foregoing and other features of the present invention will become apparent to one skilled in the art to which the present invention relates upon consideration of the invention with reference to the accompanying drawings, wherein.

DETAILED DESCRIPTION OF THE INVENTION

Referring now to FIGS. 1 to 6, embodiments of a catheter for intermittent self-conduction of urine in accordance with the present invention will be explained bellow.

Figure 1:
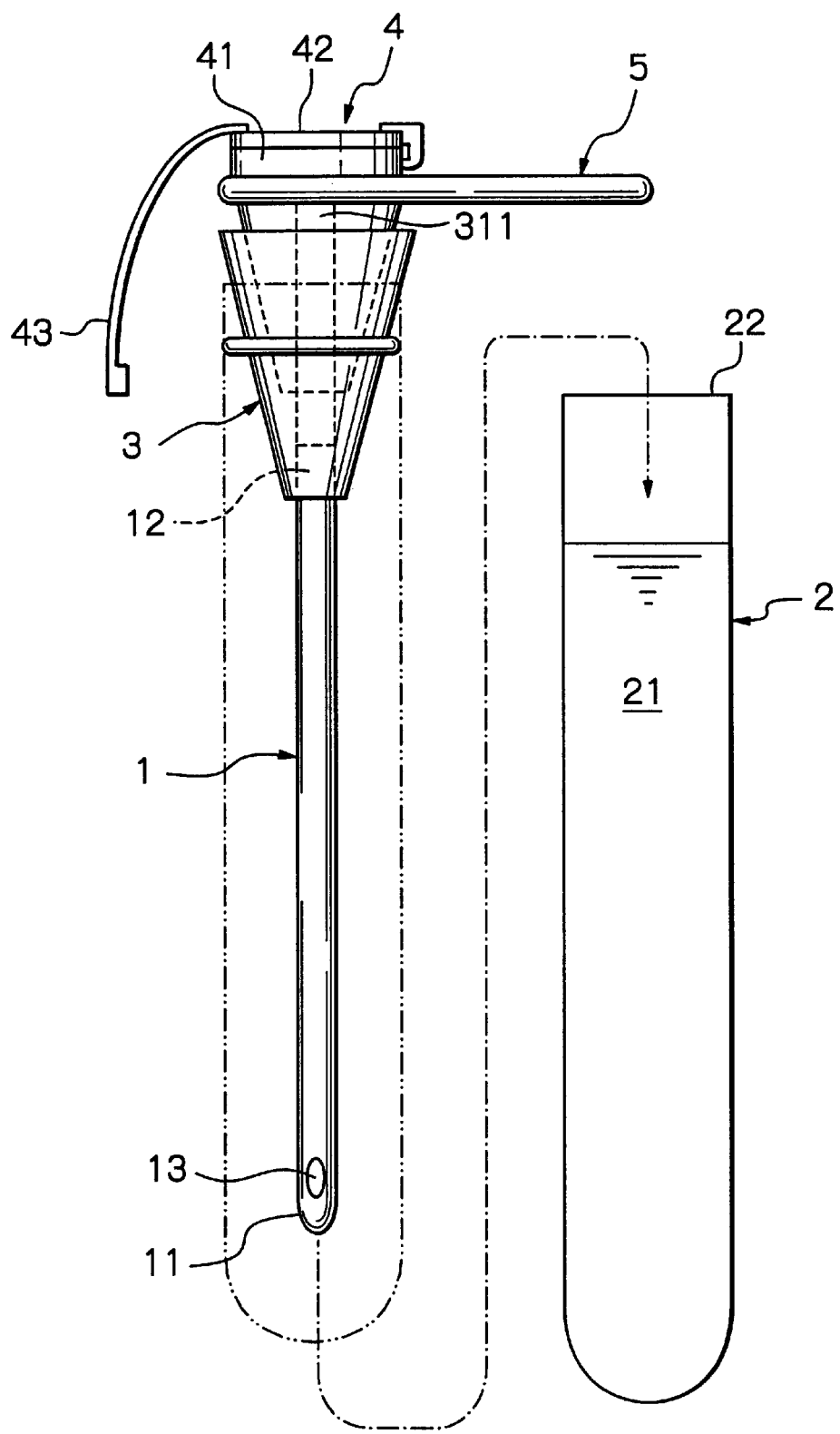
FIG. 1 is a side elevation view of an embodiment of a catheter for intermittent self-conduction of urine in accordance with the present invention.
Figure 2:
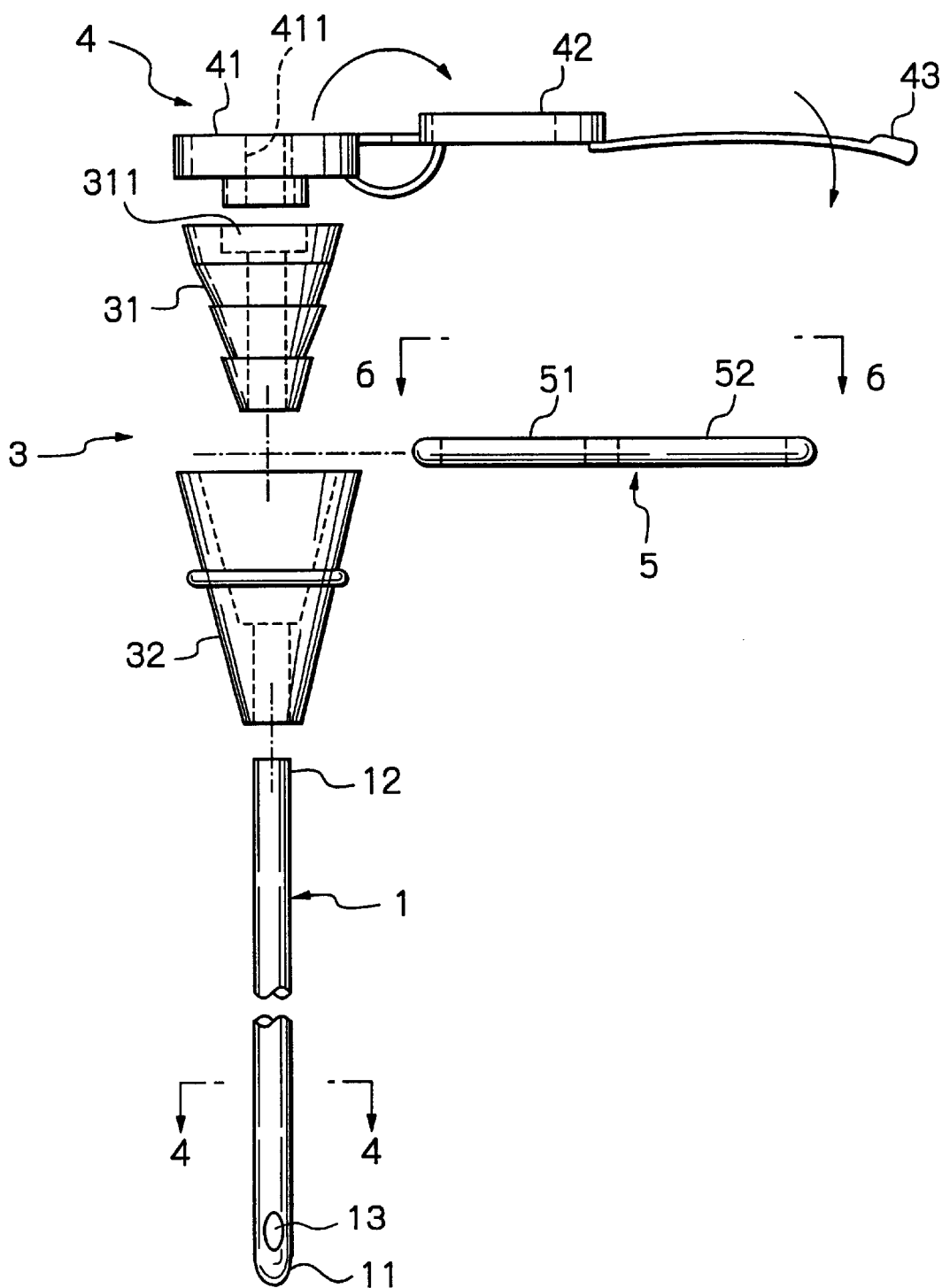
FIG. 2 is an exploded side elevation view of the catheter for intermittent self-conduction of urine shown in FIG. 1.

As best shown in FIGS. 1 and 2, a catheter for intermittent self-conduction of urine in accordance with the present invention comprises an urine conduction tube 1 having an urine conduction aperture 13 in a distal end 11 thereof, a holder 3 coupled to a proximal end 12 of the urine conduction tube 1 and adapted to be detachably engaged with an inlet port 22 of a sterilizing solution case 2 which is adapted to contain a sterilizing solution 21, and a cap 4 for closing an outlet 311 of the holder 3.

Figure 4:
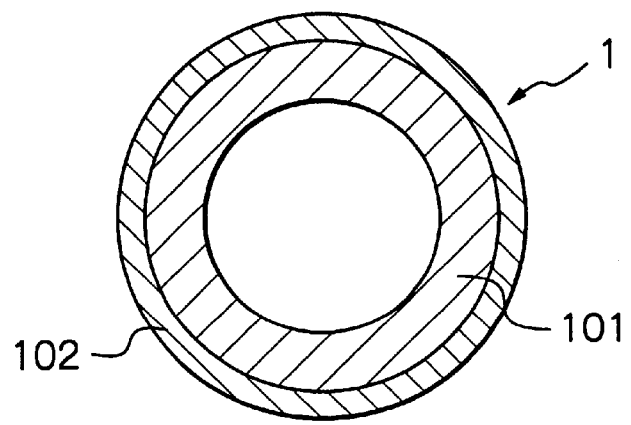
FIG. 4 is a cross sectional view of an urine conduction tube taken along line 4—4 in FIG. 2.

As shown in FIG. 4, the urine conduction tube 1 is a dual layer tube including an inner tube member 101 made of a hard synthetic resin material which is medicine-proof and an outer tube member 102 made of a soft synthetic resin material which is medicine-proof. The urine conduction tube 1 has an outer diameter of 3.0 mm to 7.0 mm and a length of 130 mm to 330 mm. The inner tube member 101 in the urine conduction tube 1 is made of a hard synthetic resin material which is medicine-proof and is selected from a group of polytetrafluoroethylene (trade name "TEFLON"), olefine base resin, polyamide base resin, and polyester base resin. The outer tube member. 102 in the urine conduction tube 1 is made of a soft synthetic resin material which is medicine-proof and is selected from a group of silicone rubber, fluororubber, and butyl rubber.

Preferably, the inner tube member made of a hard synthetic resin material which is medicine-proof has a hardness in the range of D 50 to D 90 and a thickness in the range of 0.2 mm to 2.0 mm. The catheter itself will be too hard to enter a urethra outside the ranges. The outer tube member 102 made of a soft synthetic resin material which is medicine-proof preferably has a hardness in the range of SH 10 to SH 80 and a thickness in the range of 0.2 mm to 2.0 mm. A surface of the catheter will be to soft to prevent breakage without the ranges.

Figure 6:
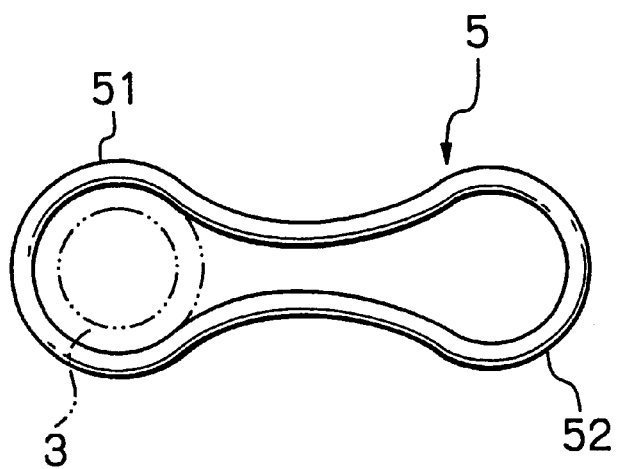
FIG. 6 is a plan view of a handle to be attached to an upper portion of the holder in the catheter for intermittent self-conduction of urine shown in FIG. 1.

As shown in FIGS. 1 and 2, the holder 3 may be provided on its upper portion with a handle 5 to be held by a user in use. As shown in FIG. 6, the handle 5 is formed into a hoop-like configuration including an engaging portion 51 and a holding portion 52. The holder 3, as shown in FIG. 2, includes an inner holder member 31 and an outer holder member 32. Both members are detachably coupled to each other (see FIGS. 1 and 2).

The engaging portion 51 of the handle 5 is slid on the inner holder member 31 from a lower end of the member 31 to an upper end of the member 31 and is clamped between the inner holder member 31 and the outer holder member 32 (see FIG. 1).

Figure 3:
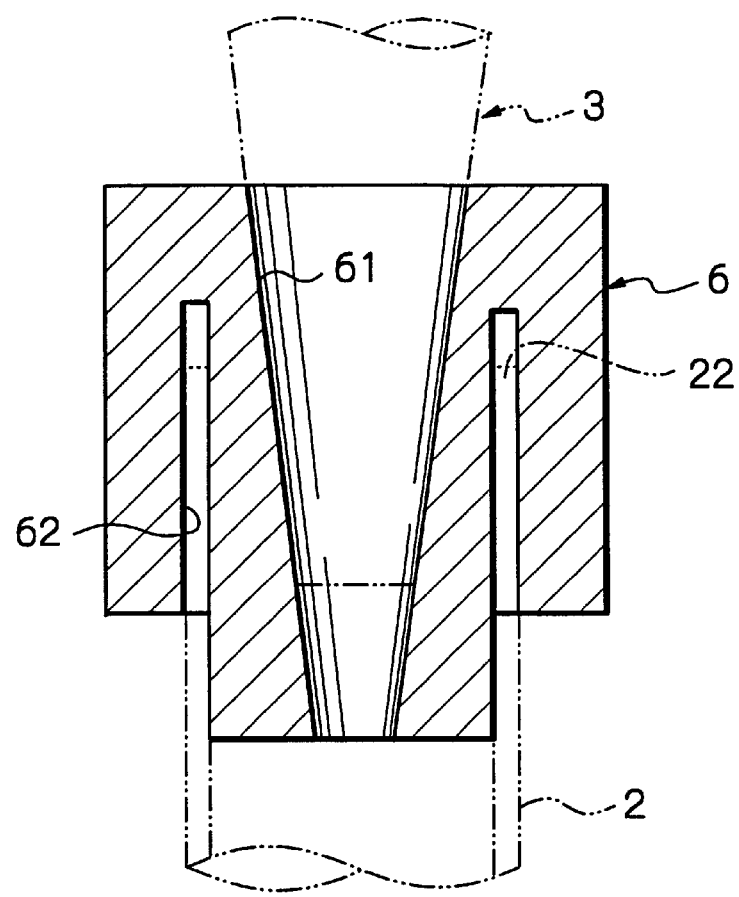
FIG. 3 is a longitudinal sectional view of a case cover to be attached to a lower portion of a holder in the catheter for intermittent self-conduction of urine shown in FIG. 1.

Also, the holder 3 may be also provided on its lower portion with a case cover 6 (see FIG. 3) which covers inner and outer surfaces of an inlet port 22 in the sterilizing solution case 2 when the urine conduction tube 1 is contained in the sterilizing solution case 2. As shown in FIG. 3, the case cover 6 is provided with a tapered opening 61 and an annular groove 62. A lower end of the outer holder member 32 is inserted into the tapered opening 61 while an inlet port 22 of the sterilizing case 2 is inserted into the annular groove 62.

As shown in FIGS. 1 and 2, the cap 4 includes a cap body 41, a lid 42, and a strap 43. The cap body 41 is fitted in an outlet 311 of the inner holder member 31 of the holder 3. The lid 42 closes an outlet 411 of the cap body 41. The strap 43 serves to help the lid to open and close the outlet 411 (see FIG. 2).

Figure 5:
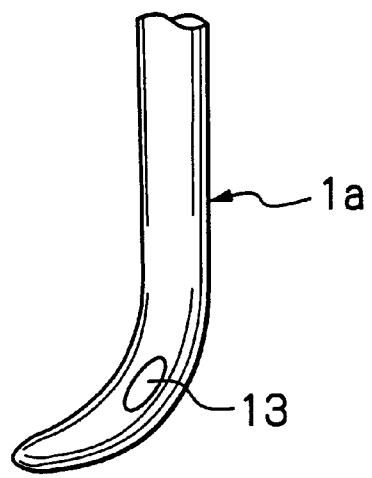
FIG. 5 is a side elevation view of a distal end of the urine conduction tube, illustrating another urine conduction tube.

As shown in FIG. 5, a urine conduction tube la may be a Martin type catheter having a curved distal end.

Since a manner of operating and using a catheter for intermittent self-conduction of urine is well known, the explanation of the manner thereof is omitted here.

According to the catheter for intermittent self-conduction of urine of the present invention, it is easy to insert the catheter into an urethra port since the urine conduction tube is relatively hard and it is possible to insert the catheter through the urethra into the bladder without inducing any pain during insertion since the surface of the urine conduction tube is relatively soft.

From the above description of the invention, those skilled in the art will perceive improvements, changes and modifications. Such improvements, changes and modifications within the skill of the art are intended to be covered by the appended claims.

The entire disclosure of Japanese Patent Application No. HEI 11-285092 (1999) filed on Oct. 6, 1999 including specification, claims, drawings and summary is incorporated herein by reference in its entirety.

What is claimed is:

1. A combination of a catheter and a sterilizing solution case, the combination comprising:

a sterilizing solution case having an inlet port; and a catheter including a urine conduction tube having (1) a distal end with inlet means for introducing urine into said urine conduction tube, and (2) a proximal end;

a holder coupled to the proximal end of said urine conduction tube, said holder detachably engaged with the inlet port of said sterilizing solution case, which is adapted to contain a sterilizing solution, said holder having an outlet; and a cap for closing the outlet of said holder;

wherein said urine conduction tube is a dual layer tube including (1) an inner tube member made of a synthetic resin material which is medicine-proof, and (2) an outer tube member made of a synthetic resin material which is medicine-proof, and wherein said outer tube member is bonded to an outside of said inner tube member, and the synthetic resin material of said inner tube member is harder than the synthetic resin material of said outer tube member.

2. The combination according to claim 1, wherein the synthetic resin material of said inner tube member is selected from the group consisting of polytetrafluoroethylene, olefine base resin, polyamide base resin, and polyester base resin, and wherein the synthetic resin material of said outer tube member is selected from the group consisting of silicone rubber, fluororubber, and butyl rubber.

3. The combination according to claim 2, wherein the synthetic resin material of said inner tube member has a shore hardness in the range of 50 to 90 on a Shore D scale, and said inner tube member has a thickness in the range of 0.2 mm to 2.0 mm, and wherein the synthetic resin material of said outer tube has a shore hardness in the range of 10 to 80 on a Shore A scale, and said outer tube member has a thickness in the range of 0.2 mm to 2.0 mm.

4. The combination according to claim 1, further comprising a handle provided on an upper portion of said holder.

5. The combination according to claim 1, further comprising a case cover provided on a lower portion of said holder, said case covering inner and outer surfaces of the inlet port of said sterilizing solution case when said urine conduction tube is contained in said sterilizing solution case.

* * * * *